US012784375B2

(12) United States Patent
Bügler et al.

(10) Patent No.: US 12,784,375 B2
(45) Date of Patent: Nov. 3, 2026

(54) APPARATUS, METHOD AND COMPUTER PROGRAM FOR PROVIDING INFORMATION RELATING TO A COGNITIVE STATE OF AN INDIVIDUAL

(71) Applicant: Altoida, Inc., Washington, DC (US)

(72) Inventors: Maximilian Bügler, Schechen (DE); Robbert Harms, Nijmegen (NL); Ioannis Tarnanas, Washington, DC (US)

(73) Assignee: Altoida, Inc., Washington, DC (US)

( * ) Notice: Subject to any disclaimer, the term of this patent is extended or adjusted under 35 U.S.C. 154(b) by 570 days.

(21) Appl. No.: 18/274,025

(22) PCT Filed: Jan. 28, 2022

(86) PCT No.: PCT/IB2022/050752
§ 371 (c)(1),
(2) Date: Dec. 6, 2023

(87) PCT Pub. No.: WO2022/162602
PCT Pub. Date: Aug. 4, 2022

(65) Prior Publication Data

US 2024/0341667 A1 Oct. 17, 2024

Related U.S. Application Data

(60) Provisional application No. 63/211,960, filed on Jun. 17, 2021.

(30) Foreign Application Priority Data

Jan. 28, 2021 (CH) .................................... 00083/21

(51) Int. Cl.
*A61B 5/11* (2006.01)
*A61B 5/00* (2006.01)
(Continued)

(52) U.S. Cl.
CPC .............. *G06T 19/006* (2013.01); *A61B 5/11* (2013.01); *A61B 5/4088* (2013.01); *G06V 10/44* (2022.01); *G06V 40/28* (2022.01); *G16H 50/20* (2018.01)

(58) Field of Classification Search
CPC ....... G06T 19/006; A61B 5/11; A61B 5/4088; G06V 10/44; G06V 40/28; G16H 50/20
See application file for complete search history.

(56) References Cited

U.S. PATENT DOCUMENTS

2020/0117889 A1* 4/2020 Laput .................... G06N 3/082

FOREIGN PATENT DOCUMENTS

CA 2923979 A1 3/2014
CA 3073111 A1 2/2019
(Continued)

OTHER PUBLICATIONS

WO, PCT/IB2022/050751 ISR and Written Opinion, May 13, 2022.
(Continued)

*Primary Examiner* — Rex R Holmes
(74) *Attorney, Agent, or Firm* — Cesari and McKenna, LLP

(57) ABSTRACT

Disclosed is an apparatus for providing information relating to a cognitive state of a first individual. The apparatus comprises a measurement unit operable to measure the first individual's hand movement in a personal axis, the personal axis being an axis from the hand to the first individual. The apparatus comprises a recording module configured to record data from the measurement unit. The apparatus comprises a machine learning module configured to provide information relating to the cognitive state of the first individual using a set of first movement data based on the data recorded by the recording module. The set of first movement data preferentially relates to movement of the hand of the
(Continued)

first individual in the personal axis over movement of the hand of the first individual in axes orthogonal to the personal axis.

17 Claims, 7 Drawing Sheets

(51) Int. Cl.

| | |
|---|---|
| ***G06T 19/00*** | (2011.01) |
| ***G06V 10/44*** | (2022.01) |
| ***G06V 40/20*** | (2022.01) |
| ***G16H 50/20*** | (2018.01) |

(56) References Cited

FOREIGN PATENT DOCUMENTS

| | | | |
|---|---|---|---|
| CN | 1111419237 | A | 7/2020 |
| CN | 119865812 | A | 4/2025 |
| EP | 3 621 276 | A1 | 3/2020 |
| WO | 2017065241 | A1 | 4/2017 |
| WO | 2019211713 | A1 | 11/2019 |
| WO | 2021009412 | A1 | 1/2021 |

OTHER PUBLICATIONS

WO, PCT/IB2022/050752 ISR and Written Opinion, May 17, 2022.

Buegler, M., et al., "Digital biomarker-based individualized prognosis for people at risk of dementia", Alzheimer's Dement., 2020, pp. 1-13.

Dutta, S., et al., "Human Cognitive State Classification Through Ambulatory EEG Signal Analysis", Advances in Databases and Information Systems, 2019, pp. 169-181.

Tarnanas, I., et al., "Can detection and prediction models for Alzheimer's Disease be applied to Prodromal Parkinson's Disease using explainable artificial intelligence? A brief report on Digital Neuro Signatures.", Open Research Europe, 2021, Version 1, pp. 1-14.

Tarnanas, I., et al., "Can detection and prediction models for Alzheimer's Disease be applied to Prodromal Parkinson's Disease using explainable artificial intelligence? A brief report on Digital Neuro Signatures.", Open Research Europe, 2022, Version 2, pp. 1-14.

* cited by examiner

APPARATUS, METHOD AND COMPUTER PROGRAM FOR PROVIDING INFORMATION RELATING TO A COGNITIVE STATE OF AN INDIVIDUAL

TECHNICAL DOMAIN

The present invention concerns an apparatus, method and computer program for providing information relating to, and optionally determining, a cognitive state of an individual, for example a user of a mobile device comprising an Inertial Measurement Unit (IMU).

RELATED ART

The detection of cognitive states, in particular of health states with respect to brain diseases or brain damages, are difficult to detect. A specialized doctor is needed, who knows the symptoms of the respective brain disease or brain damage. Even then, the detection of such health states by human doctors is not very objective and often error-prone.

In the state of the art, mobile devices are able to generate user data based on the path of the mobile device.

In this context, the expression "mobile device" preferably indicates a handheld portable device, like a smartphone or a tablet. However, this expression indicates also any other device portable by a user. For example, the mobile device can be a wearable device, for example a (smart) bracelet like a smart watch, (smart) glasses or any other (smart) device wearable by the user. A mobile device can be realized in one single device or also be realized in at least two individual or distinct devices. The at least two individual or distinct devices can for example be at least two of a portable handheld device (e.g. smartphone), a bracelet (e.g. a smart bracelet like a smart watch), glasses (e.g. augmented reality (AR) glasses) or any other device wearable by the user.

EP3621276, filed by the applicant, describes that the use of user's features recorded with a second camera of the mobile device in combination with the path of the mobile device significantly improves the detection quality for the cognitive state.

Aspects of the present invention seek to provide an improved apparatus, method and system for providing information relating to a cognitive state of an individual.

SHORT DISCLOSURE OF THE INVENTION

Aspects of the present invention seek to provide an improved apparatus, method and computer program for providing information relating to a cognitive state of an individual.

Some embodiments can further improve the quality detection of the cognitive state of a user, by using a mobile device.

According to an aspect of the present invention, there is provided an apparatus for providing information relating to a cognitive state of a first individual, the apparatus comprising:

- a measurement unit operable to measure a movement of the first individual,
- a recording module configured to record data from the measurement unit,
- a machine learning module configured to provide information relating to the cognitive state of the first individual using a set of first movement data based on the data recorded by the recording module.

According to an aspect of the invention, there is provided a method of providing information relating to a cognitive state of a first individual, including:

- using a machine learning module to provide information relating to the cognitive state of the first individual using a set of first movement data relating to a movement of the first individual.

According to an aspect of the invention, there is provided a program configured to perform the method when executed on a computing device.

According to an aspect of the invention, there is provided a computer implemented system for providing information relating to a cognitive state of a first individual, including:

- a machine learning module configured to provide information relating to the cognitive state of the first individual using a set of first movement data relating to a movement of the first individual.

According to an aspect of the invention, there is provided an apparatus for providing information relating to a cognitive state of a first individual, the apparatus comprising:

- a measurement unit operable to measure a movement of a hand of the first individual,
- a recording module configured to record data from the measurement unit,
- a machine learning module configured to provide information relating to the cognitive state of the first individual using a set of first movement data based on the data recorded by the recording module;
- wherein the apparatus is configured to require, during a measurement window, the first individual to keep the hand substantially steady and/or substantially stationary;
- wherein the set of first movement data is substantially entirely based on data relating to movement during the measurement window.

According to an aspect of the invention, there is provided a method of providing information relating to a cognitive state of a first individual, including:

- requiring, during a measurement window, the first individual to keep a hand substantially steady and/or substantially stationary;
- using a machine learning module to provide information relating to the cognitive state of the first individual using a set of first movement data relating to a movement of the hand;
- wherein the set of first movement data is substantially entirely based on data relating to movement during the measurement window.

According to an aspect of the invention, there is provided a program configured to perform the method when executed on a computing device.

According to an aspect of the invention, there is provided a computer implemented system for providing information relating to a cognitive state of a first individual, including:

- a machine learning module configured to provide information relating to the cognitive state of the first individual using a set of first movement data relating to a movement of a hand of the first individual;
- wherein the set of first movement data is substantially entirely based on data relating to movement during a measurement window in which the first individual is required to keep the hand substantially steady and/or substantially stationary.

Optional features are recited in the dependent claims, which are applicable to the above aspects of the invention.

According to an aspect of the invention, there is provided apparatus for providing information relating to a cognitive state of a first individual, the apparatus comprising:

- a measurement unit operable to measure the first individual's hand movement in a personal axis, the personal axis being an axis from the hand to the first individual,
- a recording module configured to record data from the measurement unit,
- a machine learning module configured to provide information relating to the cognitive state of the first individual using a set of first movement data based on the data recorded by the recording module, wherein the set of first movement data preferentially relates to movement of the hand of the first individual in the personal axis over movement of the hand of the first individual in axes orthogonal to the personal axis.

In some embodiments, the measurement unit is configured to measure the first individual's hand movement in the personal axis while the hand is holding an item. In one embodiment, the item is a mobile device including the measurement unit as an IMU in the mobile device. In some embodiments, the measurement unit is configured to measure the first individual's hand movement in the personal axis while the item is held in both hands of the first individual.

In some embodiments, the machine learning module is trained on sets of second movement data associated with a plurality of second individuals, each set of second movement data being associated with a particular second individual, each second individual being identified as having a medical condition or not having the medical condition, the plurality of second individuals including at least one individual identified as having the medical condition and at least one individual identified as not having the medical condition, the medical condition being Alzheimer's disease and/or Mild Cognitive Impairment, wherein each of the sets of second movement data preferentially relates to movement of a respective hand of the respective individual in a respective personal axis over movement of the respective hand in axes orthogonal to the respective personal axis, the respective personal axis being an axis from the respective hand to the respective individual.

In some embodiments, the apparatus includes a feature extraction module configured to preferentially extract, from the data recorded by the recording module, data relating to movement of the hand of the first individual in the personal axis, to form the set of first movement data.

In some embodiments, the apparatus comprises a mobile device, wherein the first individual is a user of the mobile device, and the measurement unit is an IMU in the mobile device.

In some embodiments, the IMU includes a gyroscope for measuring the orientation change of the mobile device, and the feature extraction module is configured to utilise data recorded by the recording module relating to the orientation change of the mobile device to preferentially extract, from the data recorded by the recording module, data relating to movement of the hand of the first individual in the personal axis, to form the set of first movement data.

In some embodiments, the apparatus comprises:

- optical output means in the mobile device, for optically giving out information to the user,
- a camera in the mobile device, for recording images of an environment of the mobile device.

In some embodiments, the apparatus comprises:

- an augmented reality module, for generating an augmented reality environment shown via the optical output means and based on the environment of the mobile device captured by the camera,
- an enabling module, for enabling an input element in the mobile device once the augmented reality environment is shown, said enabling depending on data measured by the IMU, said input element allowing the user to solve a task once it is selected by the user after being enabled.

In some embodiments, the recording module is configured to record data from the IMU in a period of time between the input element enablement and selection.

In some embodiments, the apparatus is configured to require, during a measurement window; the first individual to restrict all movements of the hand except in the personal axis, wherein the set of first movement data is substantially entirely based on data relating to movement during the measurement window.

In some embodiments, the apparatus is configured to require, during a or the measurement window; the first individual to keep the hand substantially steady and/or substantially stationary, wherein the set of first movement data is substantially entirely based on data relating to movement during the measurement window:

In some embodiments, the apparatus includes an output and the apparatus is configured to indicate to the first individual via the output when the first individual is required to keep the hand substantially steady and/or substantially stationary.

In some embodiments, the measurement unit includes an accelerometer and the apparatus includes an integration module configured to integrate the data recorded by the recording module resulting from the accelerometer, wherein the set of first movement data is based on the integrated data.

In some embodiments, the integration module is configured to double-integrate the data recorded by the recording module resulting from the accelerometer to result in positional data, wherein the set of first movement data is based on the positional data.

In some embodiments, the apparatus comprises a or the feature extraction module configured to reduce the data recorded by the recording module to a set of magnitudes at given frequencies, wherein the set of first movement data is based on said set of magnitudes at given frequencies.

In some embodiments, the information relating to the cognitive state of the first individual includes a prediction of future Alzheimer's disease and/or conversion from Mild Cognitive Impairment to Alzheimer's disease for the first individual.

In some embodiments, the machine learning module can be configured to determine whether or not the first individual should be receiving a drug, and/or determine the dose and frequency of drug use.

According to an aspect of the invention, there is provided a method of providing information relating to a cognitive state of a first individual, including:

- using a machine learning module to provide information relating to the cognitive state of the first individual using a set of first movement data relating to movement of a hand of the first individual, wherein the set of first movement data preferentially relates to movement of the hand of the first individual in the personal axis over movement of the hand of the first individual in axes orthogonal to the personal axis, the personal axis being an axis from the hand to the first individual.

In some embodiments, the method includes using the machine learning module to predict future Alzheimer's disease and/or conversion from Mild Cognitive Impairment to Alzheimer's disease for the first individual.

In some embodiments, the method includes measuring movement of the hand of the first individual to determine the set of first movement data.

In some embodiments, the first individual's hand movement in the personal axis is measured while the hand is holding an item. In one embodiment, the item is a mobile device including a measurement unit as an IMU in the mobile device. In some embodiments, the first individual's hand movement in the personal axis is measured while the item is held in both hands of the first individual.

In some embodiments, the method includes preferentially extracting, from data relating to the first individual's hand movement, data relating to movement of the hand of the first individual in the personal axis, to form the set of first movement data.

In some embodiments, the method includes requiring, during a measurement window, the first individual to keep the hand substantially steady and/or substantially stationary and/or requiring, during a or the measurement window; the first individual to restrict all movements of the hand except in the personal axis:

wherein the set of first movement data is substantially entirely based on data relating to movement during the measurement window.

In some embodiments, the method includes using an apparatus comprising:

the mobile device, an IMU in the mobile device, optical output means in the mobile device, for optically giving out information to the user, wherein the method comprises the following steps recording images of an environment of the mobile device, said images being taken by using a camera in the mobile device, generating an augmented reality environment shown via the optical output means and based on the environment of the mobile device captured by the camera, by using an augmented reality module of said apparatus, enabling an input element in the mobile device once the augmented reality environment is shown, said enabling depending on data measured by the IMU, said input element allowing the user to solve a task once it is selected by the user after being enabled, by using an enabling module of said apparatus, recording data from the IMU optionally in a period of time between the input element enablement and selection, by using a recording module of said apparatus.

In some embodiments, the period of time between the input element enablement and selection is the measurement window.

In some embodiments, the method includes reducing data relating to movement of the hand of the first individual to a set of magnitudes at given frequencies, wherein the set of first movement data is based on said set of magnitudes at given frequencies.

It is to be noted that the method can include performing any of the operations recited for the apparatus above.

In some embodiments, the method can include determining whether or not the first individual should be receiving a drug, and/or determining the dose and frequency of drug use.

According to an aspect of the invention, there is provided a program configured to perform the method recited above when executed on a computing device.

According to an aspect of the invention, there is provided a computer implemented system for providing information relating to a cognitive state of a first individual, including:

a machine learning module configured to provide information relating to the cognitive state of the first individual using a set of first movement data, wherein the set of first movement data preferentially relates to movement of a hand of the first individual in the personal axis over movement of the hand of the first individual in axes orthogonal to the personal axis, the personal axis being an axis from the hand to the first individual.

In some embodiments, the set of first movement data is substantially entirely based on data relating to movement during a measurement window in which the first individual is required to keep the hand substantially steady and/or substantially stationary.

The set of first movement data may be the set obtained as recited in the apparatus or method above.

In some embodiments, the computer implemented system may include any of the features of the apparatus recited above that do not interact with the first individual.

It is to be note that the computer implemented system can include any of the features, such as modules, recited for the apparatus above.

Some embodiments of the invention can detect the cognitive state of a user, by using a mobile device, in an alternative way with regard to the known solutions.

Some embodiments of the invention can efficiently and correctly detect the cognitive state of a user, by using a mobile device.

According to an aspect of the invention, there is provided an apparatus, wherein the apparatus comprises a mobile device, optical output means in the mobile device, for optically giving out information to the user, and a camera in the mobile device, for recording images of an environment of the mobile device.

In some embodiments, the apparatus further comprises an augmented reality module, for generating an augmented reality environment shown via the optical output means and based on the environment of the mobile device captured by the camera.

In some embodiments, an IMU in the mobile device is arranged for detecting the positional change of the mobile device. The IMU preferably comprises a (preferably 3-axes) accelerometer, for measuring the locational change of the mobile device, and/or a (preferably 3-axes) gyroscope, for measuring the orientation change of the mobile device.

In some embodiments, the IMU comprises a magnetometer for detecting the absolute orientation of the mobile device (based on the magnetic field of the earth). However, the IMU can comprise additionally or alternatively other modules for detecting the position, as a triangulation sensor. The triangulation sensor could measure the position based on different signals sent from satellites (e.g. GPS) or from cell phone base stations.

According to some embodiments of the invention, (measurement) data from the IMU are used for enabling a haptic input element in the mobile device, once the augmented reality environment is shown. According to some embodiments of the invention, this haptic input element allows the user to solve a task, once it is selected by the user, after being enabled by an enabling module.

In one preferred embodiment, the haptic input element is enabled when the (average) acceleration measured by the IMU is below a threshold, this threshold being for example 4.5 $m/s^2$. This acceleration is preferably an average acceleration, measured in a time window; this time window being preferably between 1.20 seconds and 1.40 seconds long, and preferably 1.28 seconds long.

In another preferred embodiment, the haptic input element is enabled (also) depending on at least one image taken by the camera, for example depending on the presence of a determined element and/or of a target position, in at least one image taken by the camera. For example and in a non-limiting way, the haptic input element is enabled if in at least one image taken by the camera there is a flat surface area.

According to some embodiments of the invention, the apparatus comprises a recording module, for recording data from the IMU in a period of time between the haptic input element enablement (by the enabling module) and selection (by the user).

According to some embodiments of the invention, the apparatus comprises a feature extraction module, for reducing the data recorded by the recording module to a set of magnitudes at given frequencies.

According to some embodiments of the invention, the apparatus comprises also a machine learning module, for determining the cognitive state of the user based on this set of magnitudes at given frequencies.

In some embodiments of the invention, it is possible to determine the cognitive state of the users holding the device as steady as possible, so as to be able to select the haptic input element. Otherwise, the haptic input element is not enabled by the enabling module.

In some embodiments, if the device is held steady or steady with relatively little motion, for example with an (average) acceleration below a threshold, then the haptic input element is enabled. When the haptic input element is enabled in such embodiments, it could be selected by the user for solving a task, for example for placing a virtual object in (or on) a target position.

The applicant has found that (measurement) data from the IMU in a period of time between the haptic input element enablement and selection are useful for determining the cognitive state of the user. Preferably, this period of time is comprised between 1.20 seconds and 1.40 seconds, and it is preferably equal to 1.28 seconds, which is approximately the average time users take to press the haptic input element after it becomes enabled. In general, the user holds the mobile device almost stationary in order to select the haptic input element, after its enablement.

The applicant has found that it is beneficial that the conditions in which the data from the IMU are recorded, are as similar as possible. That is, although the data itself will differ between user, the test design is preferably as similar as possible to ensure comparable data. This allows to determine in an efficient and correct way the cognitive state of a user. According to some embodiments of the invention, the users should hold the mobile device as steady as possible. This is preferably the case between the haptic input element enablement and selection.

Therefore, the apparatus according to some embodiments of the invention allows to further improve the detection of the cognitive state of a user.

Moreover, in some embodiments of the invention, the feature extraction module allows to reduce the amount of data used by the machine learning module, while still accurately describing the main characteristics of the original (i.e. not reduced) data.

Therefore, the apparatus according to some embodiments of the invention allows to efficiently and correctly detect the cognitive state of a user.

In one embodiment, the set of magnitudes at given frequencies comprises N frequencies, wherein N is an integer number between 7 and 15, preferably N=10. This allows to safeguard against noisy frequencies. Moreover, this number allows to balance too little and too many features. Each additional frequency in some embodiments of the invention increases the data by M values (wherein M is the product of the dimensions for each of the sensors of the IMU, times the number of the sensors, times the number of the test's objects and times the number of test runs). In this context, a test object is a (virtual) object allowing the user to solve a task in an AR environment.

For example, if there are three dimensions for each of two sensors for three objects over two test runs, then the number M of values is 36. Only using one frequency (and therefore have 36 features) has too little features for the machine learning module to separate the desired classes leading to underperformance. Using a higher number of frequencies, for example 20 frequencies (and therefore 720) features) gives a higher risk of over-fitting, again leading to underperformance. The applicant has found that a good balance is using 10 frequencies and thus 360 features.

In one embodiment, these given frequencies are all lower than 10 Hz. Again, higher frequencies are considered by the applicant too noisy to use in some embodiments. In some embodiments, the signal recorded from the IMU is a combination of actual signal with noise like electrical noise from the IMU's circuitry and mechanical noise (thermo-mechanical noise and environmental vibrational noise). These different noise sources often have high frequencies, which therefore are preferably excluded from consideration.

In one embodiment, the frequency resolution of the set of magnitudes at given frequencies is the inverse of the period of time between the haptic input element enablement and selection. For example, if this period is 1.28 seconds, then the frequency resolution of the set of magnitudes at given frequencies is 0.78 Hz.

In one preferred embodiment, those given frequencies are 0.78, 1.56, 2.34, 3.12, 3.91, 4.69, 5.47, 6.25, 7.03, 7.81. This corresponds to use the lowest 10 frequencies with a frequency resolution of 0.78 Hz.

In one embodiment, the optical output means is arranged to show the haptic input element at the same time or after showing the augmented reality environment.

In one embodiment, the apparatus further comprises a path module, configured to determine a positional path of the mobile device in the environment, and the machine learning module is arranged for determining the cognitive state of the user based also on the positional path of the mobile device, for example as determined while the user solves the task.

In one embodiment, once the user is at a predetermined distance, for example at 30 cm, to a target position, the visualization of the surrounding is augmented by the augmented reality module.

According to an aspect of the invention, there is provided a method for determining a cognitive state of a user of a mobile device, by using an apparatus comprising:

the mobile device, an IMU in the mobile device, optical output means in the mobile device, for optically giving out information to the user, wherein the method comprises the following steps recording images of an environment of the mobile device, said images being taken by using a camera in the mobile device, generating an augmented reality environment shown via the optical output means and based on the environment of the mobile device captured by the camera, by using an augmented reality module of said apparatus, enabling a haptic input element in the mobile device once the augmented reality environment is shown, said enabling depending on data measured by the IMU, said haptic input element allowing the user to solve a task once it is selected by the user after being enabled, by using an enabling module of said apparatus, recording data from the IMU in a period of time between the haptic input element enablement and selection, by using a recording module of said apparatus, reducing the data recorded by the recording module to a set of magnitudes at given frequencies, by using a feature extraction module of said apparatus, determining the cognitive state of the user based on said set of magnitudes at given frequencies, by using a machine learning module of said apparatus.

According to an aspect of the invention, there is provided a computer program for determining a cognitive state of a user of a mobile device including instructions configured to perform the following steps, when the instructions are executed on a processor of the apparatus and/or of the mobile device:

recording images of an environment of the mobile device, said images being taken by using a camera in the mobile device, generating an augmented reality environment shown via the optical output means and based on the environment of the mobile device captured by the camera, by using an augmented reality module of said apparatus, enabling a haptic input element in the mobile device once the augmented reality environment is shown, said enabling depending on data measured by the IMU, said haptic input element allowing the user to solve a task once it is selected by the user after being enabled, by using an enabling module of said apparatus, recording data from the IMU in a period of time between the haptic input element enablement and selection, by using a recording module of said apparatus, reducing the data recorded by the recording module to a set of magnitudes at given frequencies, by using a feature extraction module of said apparatus, determining the cognitive state of the user based on said set of magnitudes at given frequencies, by using a machine learning module of said apparatus.

It is to be appreciated that any of the features recited above can be used in any of the aspects of the invention.

SHORT DESCRIPTION OF THE DRAWINGS

Exemplar embodiments of the invention are described below, by way of example only, with reference to the accompanying drawings in which.

EXAMPLES OF EMBODIMENTS OF THE PRESENT INVENTION

Figure 1:
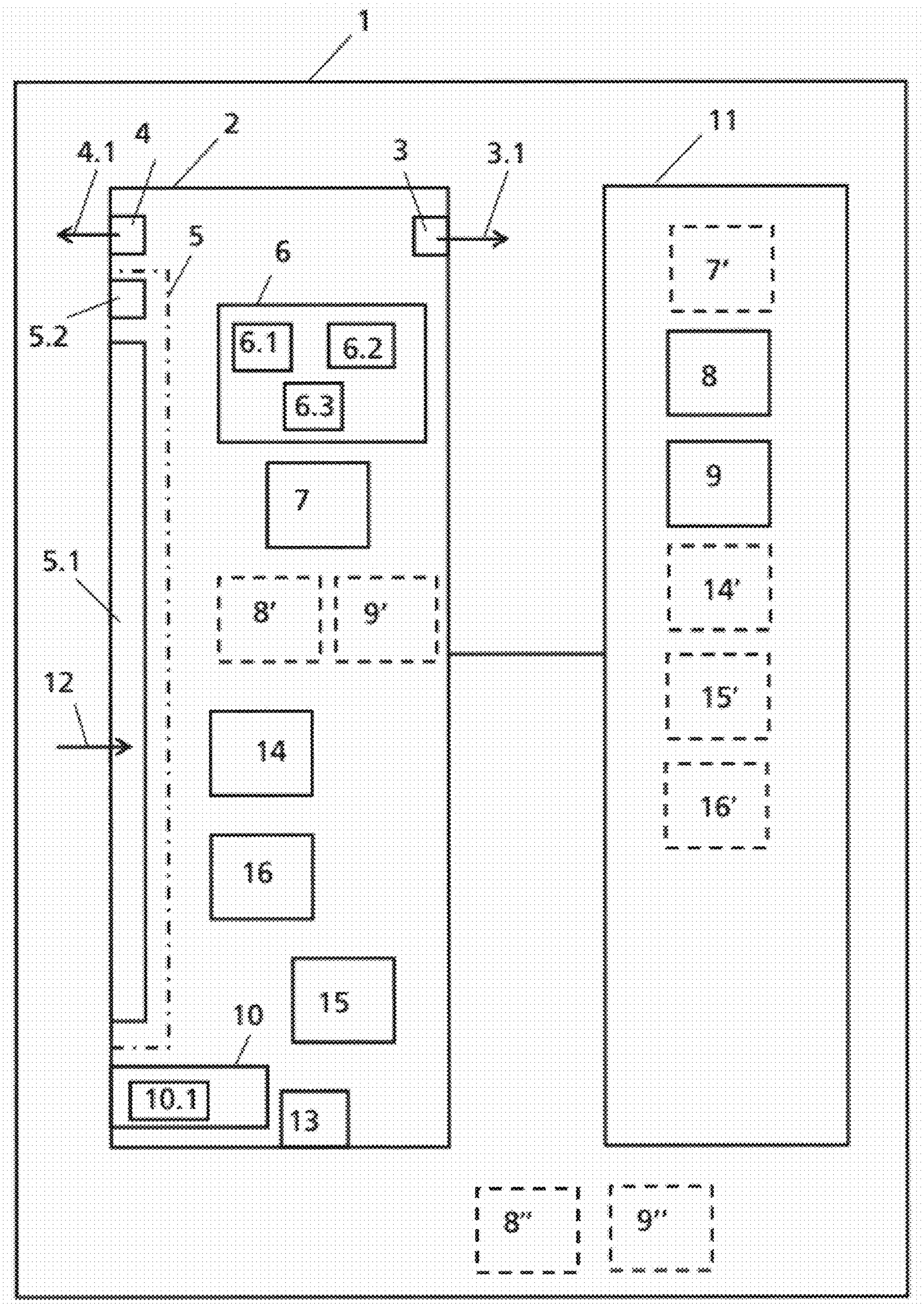
FIG. 1 shows a schematic view of an embodiment of the apparatus for determining a cognitive state of the user.

FIG. 1 shows an embodiment of an apparatus 1 for providing information relating to a cognitive state of a first individual. In this embodiment, the apparatus is for determining the cognitive state of the first individual, although in other embodiments the apparatus can simply provide information which can be used in such a determination for example by a physician.

Although connections between modules illustrated in FIG. 1 are not illustrated, at least some of the illustrated modules are (physically) connected to each other. Moreover, their arrangement in FIG. 1 is purely illustrative and not representative of their physical arrangement.

In this context, the term "module" indicates an operating unit. Some modules can be combined together, for example in a (micro)-processor. Preferably, a module is realised in a specialised chip and/or in a (not illustrated) Central Processing Unit (CPU) and/or in any other processing unit in the apparatus 1. Some modules can be formed of a plurality of operating units, each representing a part of the module. Each module can be said to include an input interface where it receives data from another module and an output interface where it provides data to another module. In some embodiments, such interfaces are provided by processing rather than being physical structures.

In the embodiment of FIG. 1, the apparatus 1 comprises a mobile device 2, a first camera 3 in the mobile device 2 for recording images of an environment of the mobile device, and a measurement unit operable to measure the first individual's hand movement in a personal axis, the personal axis being an axis from the hand to the first individual. In this embodiment, the measurement unit is an IMU 6 in the mobile device and the first individual is the user of the mobile device 2. The IMU 6 in this embodiment comprises a 3-axes accelerometer 6.1 and a 3-axes gyroscope 6.2.

The apparatus 1 comprises also an output means 5 in the mobile device 2. The output means 5 comprises optical output means 5.1 for showing the user of the mobile device 2 optical information. The optical output means 5.1 is preferably a display or screen. The optical output means 5.1, in particular the display, is preferably arranged on a second side of the mobile device 2, in particular of the handheld portable device. However, other optical output means 5.1 like a projector (e.g. an eye projector in glasses) are possible. The optical output means 5.1 is arranged in the mobile device 2, such that the user can watch the information from the optical output means 5.1 in an output view direction 12, i.e. the direction from the user to the optical output means 5.1 allowing the user to watch the information from the optical output means 5.1.

In one embodiment, the output means 5 comprises further an audio output means 5.2, like a loudspeaker, for playing back information 15 to the user.

The apparatus 1 comprises also an augmented reality module 14, for generating an augmented reality environment shown via the optical output means 5.1 and based on the environment of the mobile device 2 as captured by the camera 3.

The apparatus 1 comprises also an enabling module 15, for enabling an input element 10.1 in the mobile device 1 once the reality environment is shown via the optical output means 5.1. The input element 10.1 in the mobile device 2 is preferably a haptic input element.

In this context, the expression "haptic input element" indicates any organ or means which performs a function if it is touched by a user or by a means, such as a stylus.

In FIG. 1, the input element 10.1 belongs to the input means 10, which is configured to input user commands into the mobile device 2. The input element 10.1 is preferably a (touch) button or an element 30 displayed on a touch sensor, which is preferably arranged over the display of the mobile device 2, i.e. the display and the touch sensor constitute a touch screen. The input element 10.1 could however be a physical (linear and/or rotative) button, a mouse, a trackball, a knob or any other haptic physical element.

In another embodiment, the input element 10.1 could be also a hand or eye direction recognition module, which allows the user to solve a task. In another embodiment, the input element 10.1 could be a microphone (e.g. for voice commands). The microphone of the input means 10 could correspond to the microphone 13 described later.

According to the embodiment of FIG. 1, the input element 10.1 allows the user to solve a task on the augmented reality environment, once it is selected by the user after being enabled. This enablement is performed once the augmented reality environment is shown via the optical output means.

The enabling module 15 allows the input element 10.1 to be enabled (i.e. activated), depending on data measured by the IMU 6.

In this embodiment, the IMU 6 comprises a (3-axes) accelerometer 6.1: if the (average) acceleration measured by the accelerometer 6.1 is below a threshold, for example below 4.5 $m/s^2$, then the enabling module 15 enables the input element 10.1. Then, if a user selects the (enabled) input element 10.1, for example by touching or pressing or rotating it, the input element 10.1 allows the user to solve a task in the augmented reality environment. Otherwise, if the input element 10.1 is disabled by the enabling module 15, then if the user selects it, the user cannot solve the task in the augmented reality environment.

Since the enabling module 15 allows the input element 10.1 to be enabled depending on data measured by the IMU 6, then it is possible that the state of the input element 10.1 (enabled or disabled) changes in time, depending on those data.

For example, if the (average) acceleration measured by the accelerometer 6.1 is below a threshold, then the input element 10.1 is enabled by the enabling module 15. However, if for example the user holding the mobile device 2 starts to tremor or suddenly changes its position so that the (average) acceleration measured by the accelerometer 6.1 is above the threshold, then the input element 10.1 will be disabled by the enabling module 15. If the (average) acceleration measured by the accelerometer 6.1 comes back below threshold, then the input element 10.1 will be again enabled by the enabling module 15.

The apparatus 1 comprises also a recording module 16, for recording data from the IMU 6, and in particular for recording data from the IMU 6 in a measurement window, a period of time between the input element 10.1 enablement (by the enabling module 15) and selection (by the user). The recording module can be for example a RAM or a ROM memory.

The apparatus 1 includes an integration module (not shown) configured to integrate the data recorded by the recording module resulting from the accelerometer. In this embodiment, the integration module is configured to double-integrate the data recorded by the recording module resulting from the accelerometer to result in positional data.

The apparatus 1 comprises also a feature extraction module 8, for reducing the data recorded by the recording module 16, in particular the positional data produced by the integration module, to a set of magnitudes at given frequencies. In this embodiment, the feature extraction module 8 uses a Fast Fourier Transform for reducing the data recorded by the recording module 16, to a set of magnitudes at given frequencies.

In some embodiments, the feature extraction module 8 is also configured to preferentially extract, from the data recorded by the recording module, after it has been reduced to a set of magnitudes at different frequencies, data relating to movement of the hand of the first individual in the personal axis, to form a set of first movement data using the extracted data. In some embodiments, preferentially extracting can mean exclusively extracting. However, this extraction is not essential since, as described below, in the embodiment of FIG. 1 the user is required to hold the mobile device substantially steady and substantially stationary during the measurement window to restrict all movements of the device except in the personal axis during that time. Accordingly, the data recorded during the measurement window will typically already preferentially relate to movement of the hand of the first individual in the personal axis over movement of the hand of the first individual in axes orthogonal to the personal axis and the data recorded by the recording module can be used as the set of first movement data without extracting data relating to movement of the hand of the first individual in the personal axis. However, the preferential extraction of data by the feature extraction module can be used in addition, or in embodiments without such restrictions during a measurement window.

As a result, the set of first movement data preferentially relates to movement of the hand of the first individual in the personal axis over movement of the hand of the first individual in axes orthogonal to the personal axis. In other words, as a result of processing, nature of the task performed by the user, or manner of detection, the set of first movement data selectively emphasises movement of the hand of the first individual in the personal axis over movement of the hand of the first individual in axes orthogonal to the personal axis. In some embodiments, preferentially relating can mean exclusively relating. The inventors have discovered that movement in this axis can be particularly indicative of a cognitive state of a user.

In other embodiments, the data relating to movement of the hand of the first individual in the personal axis can be extracted before, or at the same time as, the data recorded by the recording module is reduced to a set of magnitudes at different frequencies.

In other embodiments, the measurement unit can be configured to preferentially detect movement of the hand of the first individual in the personal axis over movement of the hand of the first individual in axes orthogonal to the personal axis.

In some embodiments, the IMU 6 includes the gyroscope 6.2 for measuring the orientation change of the mobile device 2, and the feature extraction module 8 is configured to utilise data recorded by the recording module 16 relating to the orientation change of the mobile device 2 to preferentially extract, from the data recorded by the recording module 16, the data relating to movement of the hand of the first individual in the personal axis, to form the set of first movement data as described above. However, in the embodiment of FIG. 1, the gyroscope is not necessary and the personal axis is assumed to be a particular axis, in this case the z axis, of the mobile device 2.

As can be seen, the integration module integrates the data before feature extraction. However, in other embodiments, the integration can be done after the feature extraction, or even not at all. Nevertheless, integration is preferred as it can improve performance by about 5 percentage points.

The apparatus 1 comprises also a machine learning module 9, configured to provide information relating to, and in this embodiment for determining, the cognitive state of the user using the set of first movement data which, in the manner described above, is based on the data recorded by the recording module 16. In particular, the set of first movement data is based entirely on data relating to movement during the measurement window.

In the embodiment of FIG. 1, the apparatus 1 comprises also a second camera 4 in the mobile device 2, a path module 6.3, a task module 7, a (not illustrated) user feature module and a microphone 13.

Figure 3:
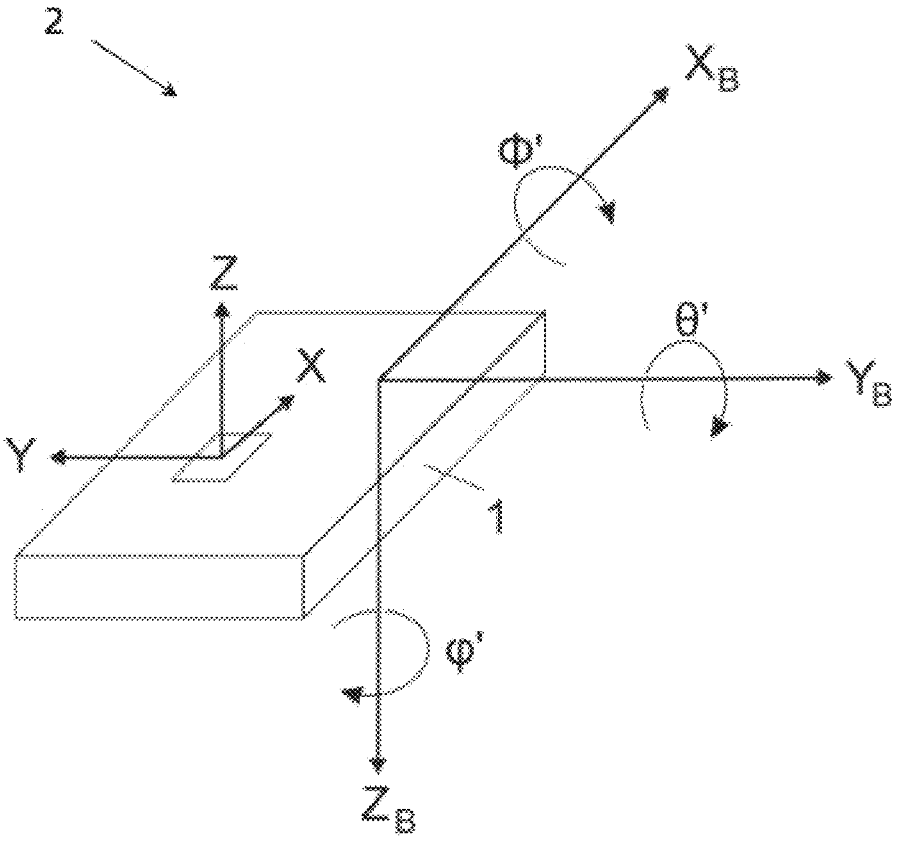
FIG. 3 illustrates a perspective view of an embodiment of a mobile device of an apparatus according to an embodiment of the invention, wherein the roll Φ', the pitch θ and the heading φ are indicated, as well as the orthogonal Cartesian axes of reference X, Y and Z.

The path module 6.3 is configured to determine the path of the mobile device 2, in particular the path which the mobile device 2 follows, while at least a part of the task is solved. In the embodiment of FIG. 3, the path module 6.3 is in the IMU 6. It is however also possible to arrange the path module 6.3 completely or partly outside the IMU 6. Preferably, the path module 6.3 is arranged in the mobile device 2.

In FIG. 1, the second camera 4 points in a second view direction 4.1 such that images in a second view direction 4.1 are recorded, as described in the patent application EP3621276, filed by the applicant. The second camera 4 is configured to record images with the user, while the user solves (at least a part of) the task with the mobile device 2. However, this is not necessary in every embodiment.

The microphone 13 is configured to record an audio signal of the environment of the mobile device 2. The microphone 13 is configured to record the audio signal of the user, while the user solves (at least a part of) the task with the mobile device 2. However, this is not necessary in every embodiment.

The (not illustrated) user feature module is configured to determine at least one user feature based on the images recorded by the further camera 4 while the user solves the task and/or in the audio signal recorded by the microphone 13 while the user solves the task. However, this is not necessary in every embodiment.

In this embodiment, the apparatus 1 comprises a further device 11 providing a computer implemented system for realising some computational work remote from the mobile device 2. In other words, the mobile device and further device are both computing devices and the processing is split between them. The further device 11 can be connected with the mobile device 2 to exchange data and/or results. The connection between the mobile device 2 and the further device 11 is preferably via internet, but can be also via WLAN, mobile phone network, other wireless communication protocols and/or other communication techniques. The further device 11 is for example a server, preferably an internet connected server and/or preferably remote from the mobile device 2. However, the further device 11 can be also arranged in the environment of the mobile device 2 and/or connected e.g. via WLAN and/or LAN and/or other wireless communication protocols. However, the further device 11 is optional and is not needed, if all computational work is done in the mobile device 2. In this case, the apparatus 1 corresponds to the mobile device 2.

For example, the task module 7, the feature extraction module 8, the machine learning module 9, the augmented reality module 14, the enabling module 15 and the recording module 16 can in some embodiments belong (totally or in part) to the further device 11 (cf relative references in FIG. 1, with a prime (') in the further device 11).

In a similar way, the feature extraction module 8 and the machine learning module 9 in FIG. 1 are illustrated as belonging to the further device 11. However, they can belong (totally or in part) to the mobile device 2 (cf relative references in FIG. 1, with a prime (') in the further device 2) or in general to the apparatus 1 (cf relative references in FIG. 1, with two primes (") in the further device 2). A similar explanation applies for the integration module (not shown).

The first camera 3 and/or the second camera 4 can be any suitable sensor for recording images of the environment, preferably of features of the environment visible to the eye of the user. Preferably, the 15 first camera 3 and/or the second camera 4 is/are an optical camera for recording images copying the environment as seen by the user. However, the first camera 3 and/or the second camera 4 can also be any other camera, e.g. 3D camera, a time of flight camera, or an optical camera covering other wavelengths than of the visible spectrum, e.g. an infrared camera or an ultraviolet camera, etc. Preferably, the first camera 3 and/or the second camera 4 comprise a digital image sensor and/or a (optical) lens (for focusing the image on the digital image sensor).

The first camera 3 is arranged in the mobile device 2 such that images of the environment of the mobile device 2 are recorded in a first view direction 3.1 and/or such that the images of the first camera 3 can be shown on the optical output means 5.1 such that, when the user looks on the optical output means 5.1 for watching the optical information of the optical output means 5.1 and an image currently recorded with the first camera 3 is shown on the optical output means 5.1, the user sees on the optical output means 5.1 the image of the environment behind the optical output means 5.1.

This environment of the mobile device 2 captured by the first camera 3 and replayed (in real time) by the optical output means 5.1 is defined here as a physical environment PE. This environment can be augmented by the augmented reality module 14 and becomes an AR environment. It can be augmented by any information or not and shall thus not be limited to the digitalised environment with augmented information.

The task module 7 is configured to interact with the user of the mobile device 2 (via the mobile device 2) by giving the user a task to solve, for example this solving making the user move (in particular walk with) the mobile device 2 in the environment of the mobile device 2. In this embodiment, the task module 7 is configured to interact with the user of the mobile device 2 (via the mobile device 2) to make the user walk with the mobile device 2 in the environment of the mobile device 2. In one embodiment, the task module 7 is configured to use the (AR) environment of the mobile device 2 in order to make the user solve the task and/or to make the user move (in particular walk with) the mobile device 2 in the (AR) environment.

In one embodiment, this task is to place a virtual object on a defined target position in the (AR) environment.

Figure 2A:
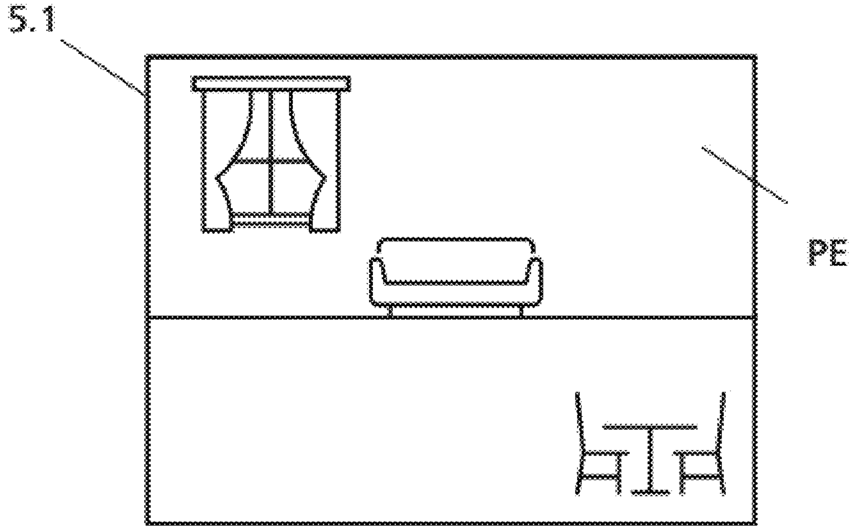
FIGS. 2A to 2D show an embodiment of a frontal view of the optical output means of the mobile device in different steps of a task solved by the user, by using the mobile device of an apparatus according to an embodiment of the invention.

FIG. 2A illustrates an example of a physical environment PE as displayed by the optical output means 5.1 of a mobile device 2 held by a user performing a test.

In this embodiment, the term "test" indicates an activity made by a user holding the mobile device 2, so as to execute at least one task in an AR environment. During at least a part of the test, the IMU 6 measures data. However, in other embodiments, the test may be an activity made by a user holding the mobile device outside an AR environment so as to execute at least one task in a non-AR environment.

In the preferred embodiment, to begin a test, the user is required to hold the mobile device 2, preferably with both of his hands and in front of his body. While doing so, the optical output means 5.1 continuously shows the output from the camera 3, preferably at the back of the mobile device 2, such that it appears as one can look through the mobile device 2.

In this embodiment, the task required is to place virtual objects on a defined target position. In this embodiment, this defined target position is near, in or on a flat surface area (e.g. a table, a chair, a floor), for example the table TP of the physical environment PE.

In this embodiment, the user should move the mobile device 2 to a predetermined distance, for example at 30 cm, to the target position TP. Since the user moves, the physical environment PE displayed on the optical output means 5.1 changes, as illustrated in FIG. 2B.

Figure 2B:
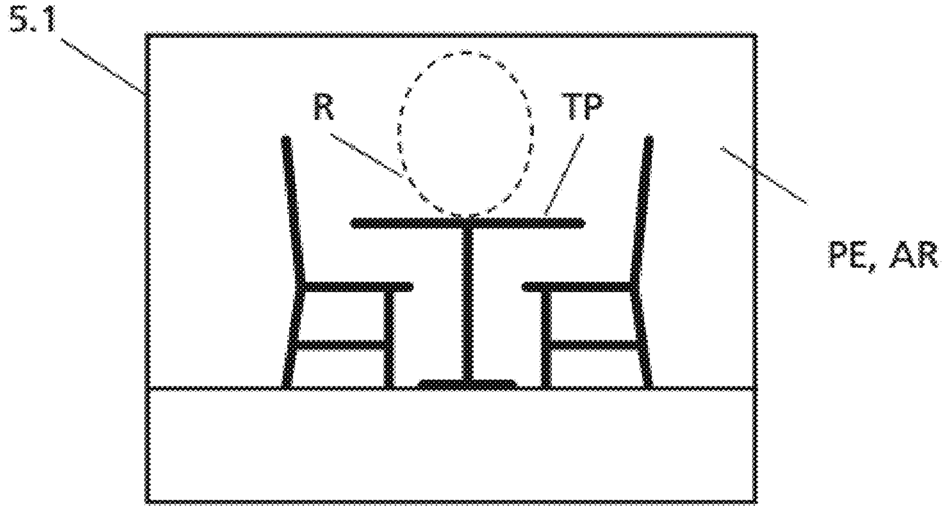

In this embodiment, once the user is at the predetermined distance, for example at 30 cm, to the target position TP, the visualization of the surrounding is augmented with a virtual element VE, for example the virtual ring shown on top of the target position TP in FIG. 2B. The virtual element (ring) VE can be displayed with a flashy colour, e.g. green.

Figure 2C:
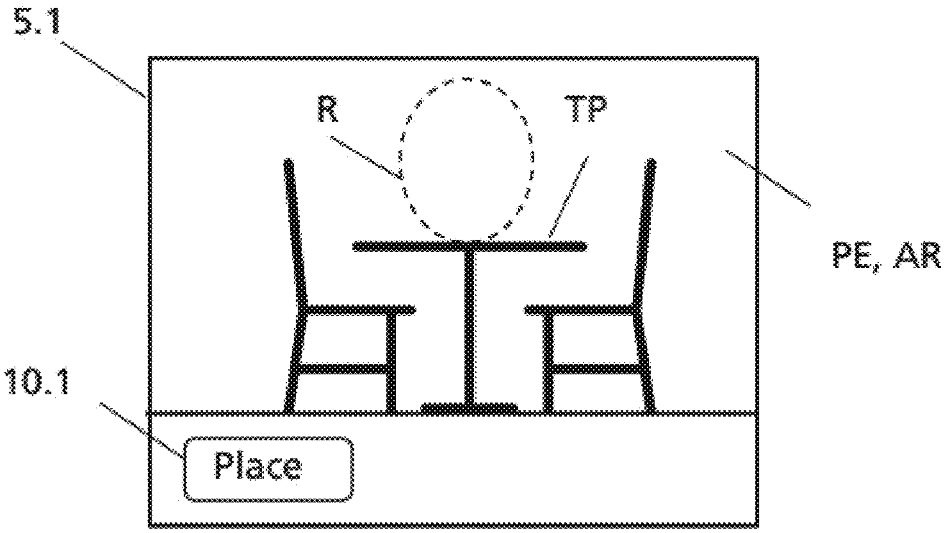

In this embodiment, once the virtual element VE is displayed, an input element 10.1, for example the virtual touch button with the text "Place" of FIG. 2C, appears. This begins the measurement window.

In this embodiment, the user is then required to hold the mobile device 2 steady to be able to select, e.g. by a touch, the input element 10.1, which ends the measurement window: If the user does not hold the mobile device 2 steady or if the mobile device 2 is moved too much, as detected by the IMU 6, then the input element 10.1 is disabled.

If the device is held steady with relatively little motion, as detected by the IMU 6, for example if the average acceleration measured by the IMU 6 is below a threshold, the input element 10.1 is enabled again, which again begins the measurement window.

Figure 2D:
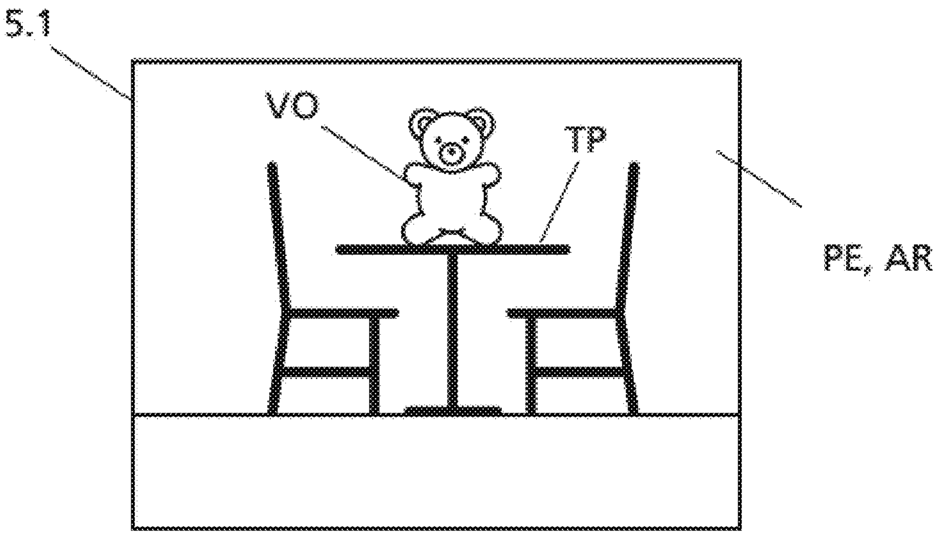

When the input element 10.1 is selected by the user, a virtual object VO (for example a little bear) is shown on the optical output means 5.1 in the position of the virtual element VE, as illustrated in FIG. 2D. Preferably, the virtual element VE and/or the input element 10.1 disappear(s).

The virtual object VO is then virtually placed and the procedure could be repeated for the other virtual objects. Preferably, no two virtual objects can be placed at the same physical location, as such, the subject is required to move a distance (for example at least one meter) from the current position to place the next virtual object. The entire test can be repeated twice, such that in total the subject placed six virtual objects over two test runs.

In one embodiment, for each of the two test runs, for each of the three objects, data from the accelerometer 6, 1 and the gyroscope 6.2 are recorded by the recording module 16 with three dimensions each. In total, this leads to 36 independent time series.

The applicant has found that (measurement) data from the IMU 6 in a period of time between the haptic input element 10.1 enablement and selection, that is during the measurement window; are useful for correctly determining the cognitive state of the user. Preferably, this period of time is comprised between 1.20 seconds and 1.40 seconds, and it is preferably equal to 1.28 seconds, which is approximately the average time users take to press the haptic input element 10.1 after it becomes enabled. The user must hold the mobile device 2 almost stationary in order to select the haptic input element 10.1.

The applicant has found beneficial for correctly determining the cognitive state of the user, that the conditions in which the data from the IMU 6 are recorded is as similar as possible. That is, although the data itself will differ between users, the test design is preferably as similar as possible to ensure comparable data.

As can be seen, the apparatus requires the user to hold the mobile device 2, and therefore their hands, stationary and as steady as possible during the measurement window, thereby restricting all movements except in the personal axis during this time. The inventors have found that this is beneficial for correctly determining the cognitive state of the user.

In this embodiment, accelerometer data is recorded at a frequency of 100 Hz, in units of $m/s^2$, for three dimensions, or axes, x, y and z, each relative to the device. FIG. 3 shows a perspective and schematic view of the mobile device 2 of the apparatus 1, and illustrates those different axes. Independent of the current position of the mobile device 2, a positive value for the x-axes implies acceleration towards the right side of the mobile device 2, a positive value for the y-axes implies acceleration towards the top of the mobile device 2, and a positive value for the z-axes implies movement perpendicular to the optical output means 5.1 in the optical output means' direction. Negative values indicate acceleration in the opposite direction. Preferably, all values are assumed to exclude the gravity component, such that when the device is held still, all axes measure a magnitude of zero.

In this embodiment, gyroscope data is recorded at a frequency of 100 Hz, in radians for rotations around each of the previously defined axes. As illustrated in FIG. 3, pitch θ records rotations around the device's x axis, roll Φ reports rotations around the y axis, and yaw φ reports rotations around the z axis. A yaw of 0 implies the phone is facing north. A pitch and roll of 0 implies the phone is lying flat. A positive roll implies a tilt to the 20 right. A positive pitch implies a forward tilt.

In this embodiment, the recording module records the data into a CSV file (Comma Separated Values, a tabular file format with on each row a new registration and columns separated by commas) with timestamps in milliseconds and other values are registered by the sensor. In addition, events during the test are registered separately in an event registration file.

Accelerometer CSV: gravity acceleration vectors with columns "timestamp,x,y,z". All accelerations are in multiples of g, so a value of 1 implies an acceleration of 9.81 $m/s^2$. The data is recorded at a sampling rate of 100 Hz. in all three dimensions. A positive value for x implies acceleration towards the right side of the mobile device 2, a positive y value implies acceleration towards the top of the mobile device 2 and a positive z value implies movement perpendicular to the optical output means 5.1 (the screen in this embodiment) in the screen's direction.

Example Data:

timestamp,x,y,z
1582207960462, −0.0028343051671999996, 0.0032169818878000004, −0.0406328439713
1582207960472, 0.0002601742744, 0.007241010665899999, −0.0436691045761
1582207960482, 0.011663720011700001, 0.017454385757400003, −0.0452742576599
1582207960492, 0.018144294619599998, 0.0211092829704, −0.044560074806199994

Gyroscope CSV: time series of attitude vectors, with columns "timestamp,pitch,roll,yaw". All angles are in radians. Pitch reports rotations around the device's x axis, roll reports rotations around the y axis, and yaw reports rotations around the z axis. The data is recorded at a sampling rate of 100 Hz. in all three dimensions. A yaw of 0 implies the phone is facing north. A pitch and roll of 0 implies the phone is lying flat. A positive roll implies a tilt to the right. A positive pitch implies a forward tilt (turning the nose down).

Example Data:

timestamp,pitch,roll,yaw
1582207960462, 0.5281299643038, 0.142492084745, −0.0383408686236
1582207960472, 0.5282309817066, 0.14270043589189998, −0.033708562147499996
1582207960482, 0.5335807962207, 0.1314814746114, −0.0280935035518
1582207960492, 0.5334306018221, 0.1286333107537, −0.05269055533250001

Event registration: events during the test are registered in an XML (extensible Markup Language, a file format for structuring relational data) file, which contains timestamps for important events. For example, when placing an object, a section is added to this file stating:

```
<place_object start_ts="1582207960462" end_ts="1582207960492"
object_name="alarm">
  <events>
    <place_button_enabled ts="1582207960462"/>
  </events>
</place_object>
```

This snippet of XML states that the subject was placing a virtual object during the timestamps start_ts="1582207960462" and end_ts="1582207960492". The object being placed was the "alarm". During this placement phase, there was one event, namely the object placement button was enabled (place_button_enabled), allowing the subject to place a virtual object. The timestamps in this document can be linked to timestamps in the accelerometer and gyroscope CSV files.

Of course the file type and format of data and event recordal can be varied in other embodiments.

The analysis of the recorded data according to this embodiment follows a multi-step procedure. First, the data is double integrated by the integration module. Second, the dimensionality of the data is reduced by the feature extraction module 8. Optionally, data relating to movement of the hand of the first individual in the personal axis is preferentially extracted to form the set of first movement data using the extracted data. Then, the set of first movement data is used in the machine learning module 9, for example to predict the chance at Alzheimer's or the chance of conversion from MCI to Alzheimer's.

As indicated above, the order of the steps can be changed in other embodiments.

Given the accelerations from the device (in this embodiment 1.28 seconds before virtual object placement, and therefore 128 samples), the integration module applies a cumulatively integration using the composite trapezoidal rule twice to go from accelerations to position.

The feature extraction module 8 allows to reduce the amount of data used by the machine learning module, while still accurately describing the main characteristics of the original (i.e. not reduced) data. It converts 'raw' data into 'features'.

In this embodiment, the feature extraction module 8 uses a Fourier transform, in particular a Fast Fourier Transform, for reducing the data recorded by the recording module to a set of magnitudes at given frequencies.

In this embodiment, the set of magnitudes at given frequencies comprises N frequencies, wherein N is an integer number between 7 and 15: in this embodiment N=10. This allows to safeguard against noisy frequencies. Moreover, this number allows to balance too little and too many features. Each additional frequency increases the data by M values (wherein M is the product of the dimensions for each of the sensors of the IMU with the number of the sensors, the number of the test's objects and the number of test runs). For example, if there are three dimensions for each of two sensors for three objects over two test runs, then the number M of values is 36. Only using one frequency (and therefore have 36 features) has too little features for the machine learning module to separate the desired classes leading to underperformance. Using an higher number of frequencies, for example 20 frequencies (and therefore 720 features) gives a higher risk of over-fitting, again leading to underperformance. The applicant has found a good balance at 10 frequencies and thus 360 features.

In this embodiment, these given frequencies are all lower than 10 Hz. Again, higher frequencies are considered by the applicant too noisy to use. The signal recorded from the IMU is a combination of actual signal with noise like electrical noise from the IMU's circuitry and mechanical noise (thermo-mechanical noise and environmental vibrational noise). These different noise sources often have high frequencies, which therefore are excluded from consideration.

In this embodiment, the frequency resolution of the set of magnitudes at given frequencies is the inverse of the period of time between the haptic input element enablement and selection. For example, if this period is 1.28 seconds, then the frequency resolution of the set of magnitudes at given frequencies is 0.78 Hz.

In this embodiment, those given frequencies are 0.78, 1.56, 2.34, 3.12, 3.91, 4.69, 5.47, 6.25, 7.03, 7.81.

For the non-integrated frequency features the feature extraction module iterates over all the AR tests, virtual objects, sensors and axes and computes for each axis of each sensor the absolute FFT (Fast Fourier Transform) features.

From those, the first 10 magnitudes are copied.

In pseudocode, we can write the following:

```
def get_placement_start_time(ARTest, VirtualObject):
  # return the "ts" property of the right <place_button_enabled /> tag.
def get_placement_end_time(ARTest, VirtualObject):
  # return the "end_ts" property of the <place_object> tag
def get_subset(Sensor, start_timestamp, end_timestamp):
  # get a subset of all the rows of the Sensor between the start timestamp
```

-continued

```
and the end timestamp.
def get_sensor_data(ARTest, VirtualObject, Sensor):
  start_timestamp = get_placement_start_time(ARTest, VirtualObject)
  end_timestamp = get_placement_end_time(ARTest, VirtualObject)
  return get_subset(Sensor, start_timestamp, end_timestamp)
frequency_features = list( )
for ARTest in [1, 2]:
  for VirtualObject in [1, 2, 3]:
    for Sensor in ['accelerometer', 'gyroscope']:
      sensor_readings = get_sensor_data(ARTest, VirtualObject,
      Sensor)
      for axis in ['x', 'y', 'z']:
        magnitudes = abs(fft(sensor_readings[axis]))
        selected_magnitudes = magnitudes[1:11]
        frequency_features.append(magnitudes)
```

The first few lines specify auxiliary functions to load the correct data. We then create an empty list for all the computed frequency features. Next, we iterate over the ARTests, the VirtualObjects (3 for each AR test) and the Sensors. At the time we load the sensor readings for each sensor by looking at the timestamps of occurrence in the event XML file, and load the data in the correct timestamp range from the raw data. Then, on those sensor readings, we apply on each axis (sensor_readings[axis]) an FFT function (fft(sensor_readings[axis])) and take the absolute numbers in that range (abs(fft(sensor_readings[axis]))). We then select the first 10 frequencies (from index 1 up to and not including 11) and append these frequencies to the list of frequency features.

The integrated frequency features are computed in a similar fashion as the non-integrated frequency features, except that we only apply it on the accelerometer data and we first integrate the accelerometer data.

In pseudocode, we get:

```
  frequency_features = list( )
  for ARTest in [1, 2]:
    for VirtualObject in [1, 2, 3]:
      sensor_readings = get_sensor_data(ARTest, VirtualObject,
      'accelerometer')
      for axis in ['x', 'y', 'z']:
        positions = cumtrapz(cumtrapz(sensor_readings[axis]))
        magnitudes = abs(fft(positions))
        selected_magnitudes = magnitudes[1:11]
        frequency_features.append(magnitudes)
```

This is similar to before, except we don't need to loop over the sensors, we only use the accelerometer. The line "cumtrapz(cumtrapz(sensor_readings[axis]))" takes the data at the indicated axes and integrates it over time twice using the composite trapezoidal rule (this is done by the integration module as described above). This gives positioning data relative to the starting point of the data subset. From that, we again compute the absolute FFT magnitudes and save those in the list of frequency features.

The non-integrated frequency features consist of 360 frequency magnitudes (ten frequencies*three dimensions*two sensors*three objects*two AR tests). Each of these magnitudes is a positive number indicating the magnitude of that particular frequency as present in the signal coming from the accelerometer or gyroscope.

As an example, for one virtual object placing of one AR test, for the X coordinate of the accelerometer we could get a set of features:

[1.654, 0.059, 0.011, 0.0523, 0.0666, 5.779, 0.194, 3.4358, 1.4534, 2.5343]

For the y-coordinate we would get a similar set of numbers, same for the z-coordinate, and then the same for the gyroscope data, etc.

The above numbers represent the frequency magnitudes of frequencies present in the data, each at the pre-specified frequencies:

[0.78, 1.56, 2.34, 3.12, 3.91, 4.69, 5.47, 6.25, 7.03, 7.81] Hz

Since these are computed directly from the raw accelerometer and gyroscope data, these frequencies are rates of change of accelerations and rotations.

The integrated frequency features are computed differently, and are computed only for the accelerometer data. Beyond that, they are similar to the above in most aspects. Since we don't compute these for the gyroscope, we only have 180 features here. Each feature again represents the magnitude of frequency in the timeseries data, again at the frequencies:

[0.78, 1.56, 2.34, 3.12, 3.91, 4.69, 5.47, 6.25, 7.03, 7.81] Hz

The major difference between the non-integrated frequency features is that these features are computed on double integrated accelerations data, i.e. relative positioning data. This makes the frequencies the rate of change in position (not in acceleration).

In some embodiments, as described above, the feature extraction module can preferentially extract data relating to movement of the hand of the first individual in the personal axis to form the set of first movement data. However, in the embodiment of FIG. 1 this is not necessary as the data already preferentially relates to such movement as a result of substantially entirely relating to movement during the measurement window.

The data from the feature extraction module is the set of first movement data on which the machine learning module operates.

Turning to the machine learning module, the expression "machine learning module" indicates a module which needs to be trained in order to learn i.e. to progressively improve a performance on a specific task.

The machine-learning module in a preferred embodiment is a neural network module, i.e. a module comprising a network of elements called neurons. Each neuron receives input and produces an output depending on that input and an "activation function". The output of certain neurons is connected to the input of other neurons, thereby forming a weighted network. The weights can be modified by a process called learning which is governed by a learning or training function.

Although the neural network module is a preferred implementation of the machine-learning module, the system according to the invention is not limited to the use of a neural network module only, but could comprise other types of machine-learning modules, e.g. and in a non-limiting way machine-learning modules arranged to implement at least one of the following machine-learning algorithms: decision trees, association rule learning, deep learning, inductive logic programming, support vector machines, clustering, Bayesian networks, reinforcement learning, representation learning, similarity and metric learning, sparse dictionary learning, genetic algorithms, rule-based machine-learning, learning classifier systems.

In one embodiment, the neural network module is a deep neural network module, e.g. it comprises multiple hidden layers between the input and output layers, e.g. at least three layers.

In one preferred embodiment, it comprises three hidden layers, each layer having a different number of neurons. In one embodiment, the number of neurons of the hidden layers decreases from the input to the output.

In the embodiment of FIG. 1, the machine learning module 9 is arranged to execute a XGBoost classification algorithm to learn the difference between the IMU readings from healthy users and those with an underlying condition.

In this example, data of a first number (e.g. 381) subjects having mild cognitive impairment (MCI) are collected together with an amyloid beta positive biomarker, and data of a second number (e.g. 1277) subjects without such cognitive impairment (yet possibly having the biomarker) are collected as well.

In other words, the machine learning module 9 is trained on sets of second movement data associated with a plurality of second individuals, each set of second movement data being associated with a particular second individual, each second individual being identified as having a medical condition or not having the medical condition, the plurality of second individuals including at least one individual identified as having the medical condition and at least one individual identified as not having the medical condition, the medical condition being Mild Cognitive Impairment or Alzheimer's disease (although in other embodiments it can be/include other medical conditions such as dementia or delirium or specific sub-types of dementia or delirium), wherein each of the sets of second movement data preferentially relates to movement of a respective hand of the respective individual in a respective personal axis over movement of the respective hand in axes orthogonal to the respective personal axis, the respective personal axis being an axis from the respective hand to the respective individual.

Data of the first number of MCI subjects as the "At Risk" class and the group of the second number of subjects as the "healthy" class. From this a feature matrix X is created, with as columns the features and as rows the first plus second number of subjects, and a separate vector y with for each subject an integer value indicating if the subject is in the class healthy (value 0) or in the class at risk (value 1). The goal is to learn a mapping from X to Y such that when a new subject is presented the machine learning module can predict the corresponding class label.

Figure 4:
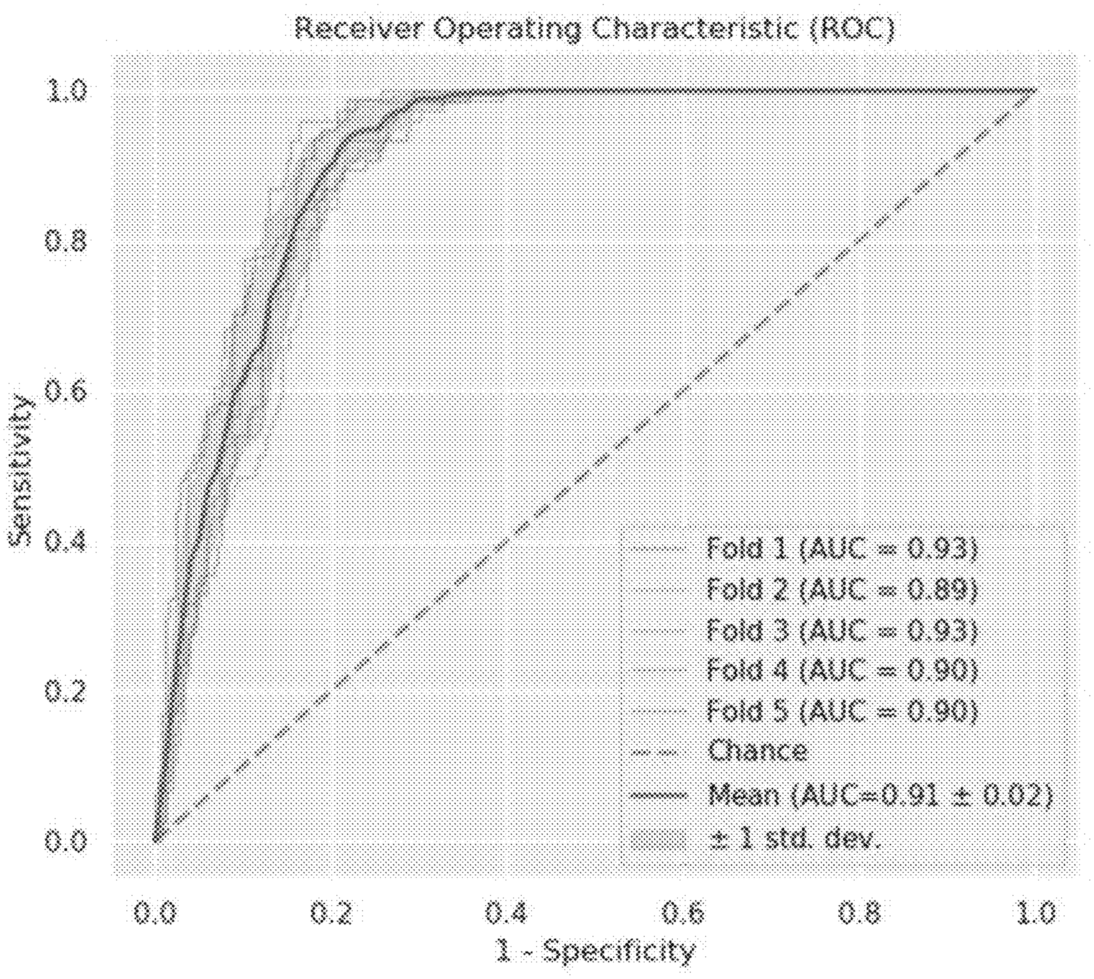
FIG. 4 is a graphic showing five-fold stratified cross-validation ROC (Receiver Operating Characteristic) performance of a classifier predicting a subject's risk of Alzheimer's, by using an embodiment of the invention.

The final classification model is an XGBoost model, trained using all data in X and Y. To assess the accuracy of this final model, a number (for example five) additional models can be trained using a (5-)fold stratified cross validation method. FIG. 4 shows the resulting Receiver Operating Characteristic (ROC) curve for an embodiment according to FIG. 1 using 381 MCI subjects and 1277 healthy subjects. The average Area Under this Curve, the ROC-AUC, is 0.91+−0.02.

In one embodiment, the machine learning module 9 allows also to determine the health state of the brain of the user, i.e. a brain disease or a brain damage. Examples for such brain diseases or brain damages are: Alzheimer's disease and/or preclinical Alzheimer's pathological change, frontal temporal dementia, traumatic brain injury, e.g. concussion, Parkinson's, Post-Operative Cognitive Disorder, Posterior Cortical Atrophy, Movement Disorders, Neurodegeneration disorders, Cognitive Impairment, Depression.

For example, given the above set of frequency features for a range of subjects we can proceed to build a classification method. To do so, we create a CSV file with as columns the frequency metrics (either the non-integrated, integrated, or both) and with one row per subject. We call this matrix X and it would look like:

X:

SubjectId, Frequency Feature_1, Frequency Feature_2, . . . , Frequency Feature_N
1, 1.654, 0.059, . . . , 0.011
2, 0.0523, 0.0666, . . . , 2.534
3, 5.779, 0.194, . . . , 1.4534
. . .

In combination we have a CSV file storing only the disease status of a person, i.e. (future) Alzheimer or healthy, we call this y and it looks like:

y:

SubjectId, DiseaseStatus
1, Healthy
2, Alzheimer's disease (AD)
3, Healthy
. . .

Given data X and status y we train an XGBoost model:

model=xgboost(X, y)

Given that model we can predict the disease status of a new subject as:

x_new_subject=[2.343, 1.662, . . . , 3.222]

y_prediction=model.predict(x_new_subject)

Where x_new_subject, are the frequency features of a subject not previously seen before.

In the embodiment of FIG. 1, the cognitive state of the user is provided by the machine learning module and given out from the apparatus 1. In this embodiment, the cognitive state of the user is given out via the output means 5 of the mobile device 2. However, in other embodiments, the cognitive state of the user can be given out from other outputs, for example to a clinician remote from the mobile device 2.

In the embodiment of FIG. 1, the cognitive state of the user is a prediction of future Alzheimer's disease and/or conversion of MCI to Alzheimer's disease. However, in other embodiments, the cognitive state can relate to the presence of Alzheimer's disease and/or the susceptibility to or the presence of other medical conditions, such as a brain disease or a brain damage, preclinical Alzheimer's pathological change, frontal temporal dementia, traumatic brain injury, e.g. concussion, Parkinson's, Post-Operative Cognitive Disorder, Posterior Cortical Atrophy, Movement Disorders, Neurodegeneration disorders, Cognitive Impairment, Depression.

Although in this embodiment the apparatus determines and outputs the cognitive state of the user, in other embodiments, the apparatus can simply provide information relating to the cognitive state. In such embodiments, the apparatus can perform the same machine learning procedure, but rather than the machine learning module determining the cognitive state, it can simply provide information relating to the cognitive state, for example a numerical score or a classification, which can be output and then used by a physician, possibly in combination with other factors, to make a determination as to cognitive state.

The apparatus can be used to determine whether or not someone should be receiving a drug (esp. for AD), and/or to determine the dose and frequency of drug use. This can for example be determined by the machine learning module and output by the apparatus.

Although in the above embodiment, the apparatus includes an integration module that integrates data, this is not necessary in every embodiment. Results from an example that did not include an integration module are shown in FIG. 5.

In this example, the machine learning module performed as described above except that, for training, data of 372 subjects having mild cognitive impairment (MCI) were collected together with an amyloid beta positive biomarker, and data of 1296 subjects without such cognitive impairment (yet possibly having the biomarker) were collected as well. FIG. 5 shows the resulting Receiver Operating Characteristic (ROC) curve for an embodiment according to FIG. 1. The average Area Under this Curve, the ROC-AUC, is 0.78+−0.02.

Figure 5:
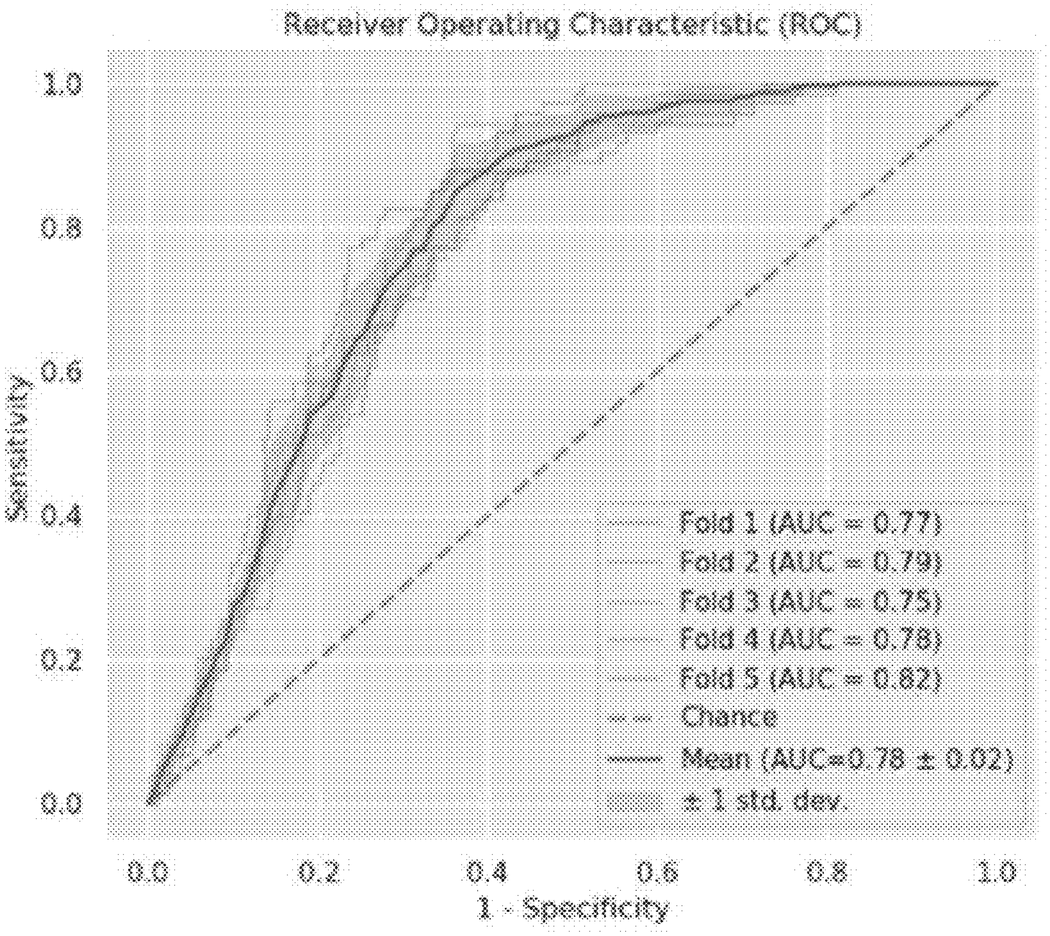
FIG. 5 is a graphic showing five-fold stratified cross-validation ROC (Receiver Operating Characteristic) performance of a classifier predicting a subject's risk of Alzheimer's, by using an embodiment of the invention.

As can be seen from a comparison of FIGS. 4 and 5, the result is good with or without integration, but better where integration is used.

Although embodiments described above are in the context of a test in an AR environment, this is not necessary in every embodiment. For example, the test can be performed without superimposing virtual objects onto an image of the physical environment. For example, another embodiment of the invention, to which FIG. 6 relates, corresponds to the embodiment of FIG. 1 but in which for example the augmented reality module 14 and the enabling module can be omitted.

Figure 6:
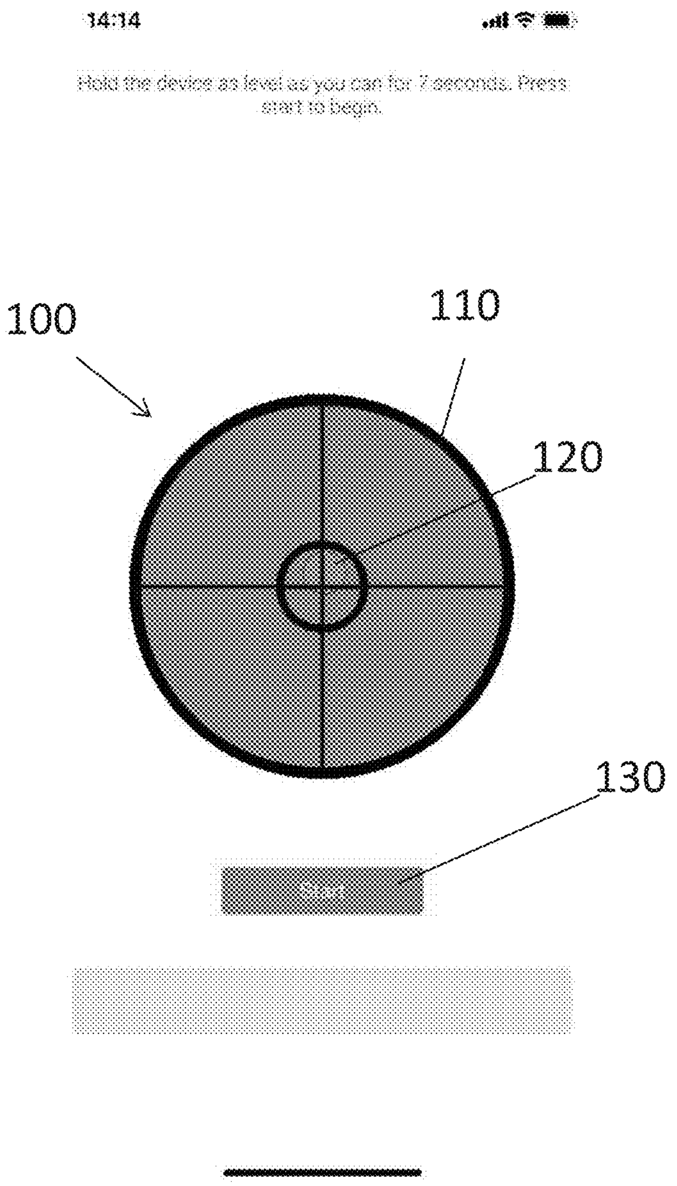
FIG. 6 is a screenshot of a mobile device according to an embodiment of the invention.

In the embodiment of FIG. 6, the task module 7 is again configured to interact with the user of the mobile device 2 by giving the user a task to solve. In this embodiment, the task requires the user to keep his/her hands substantially steady and substantially stationary during a measurement window. In this embodiment, the input element 10.1 is operable to begin the measurement window, for example by the user actuating a 'start' button 130 shown in the screenshot of FIG. 6. In other embodiments, the measurement window can be begun in different ways, optionally automatically. In the embodiment of FIG. 6, the measurement window ends automatically after a predetermined period of time, preferably between 5 and 10 seconds, in this embodiment after 7 seconds. However, in other embodiments, the measurement window can end in other ways, for example after action taken by the user.

In the embodiment of FIG. 6, the apparatus requires the user to keep his/her hands substantially steady and substantially stationary by the task module 7 being configured to cause the display of the mobile device 2 to display a level indicator and to require the user to keep the level indicator indicating that the device is level during the measurement window. In the embodiment of FIG. 6, the level indicator is a bubble level 100 and includes a fixed target 110 and a movable bubble 120. The task module 7 is configured to move the location of the bubble 120 relative to the target 110 in dependence on data from the IMU. The task module 7 is configured to require the use to keep the bubble 120 at the centre of the fixed target 110 during the measurement window, thereby requiring the user to keep the device horizontal and his/her hands steady and stationary during the measurement window; although in other embodiments the user can be required to keep the device vertical. In some embodiments, the user may be holding the mobile device 2 with one hand, but preferably the user will be required to hold the mobile device 2 with both hands.

Data relating to movement during the measurement window is recorded and processed as per the embodiment of FIG. 1. As described above, because the user is keeping his/her hands substantially steady and substantially stationary during the measurement window, the data will preferentially relate to movements in the personal axis.

Of course in some embodiments of the invention, it is possible for the apparatus to include all of the feature of the embodiments of FIGS. 1 and 6 and be configured to perform the tests of both embodiments.

Although in embodiments described above the feature extraction module allows to reduce the amount of data used by the machine learning module, while still accurately describing the main characteristics of the original (i.e. not reduced) data, it is not necessary to reduce the data in this way in every embodiment.

Although the applicant has found that (measurement) data from the IMU 6 in the measurement window while the mobile device is held substantially steady and stationary are useful for correctly determining the cognitive state of the user because hand movements in such conditions automatically preferentially relate to the personal axis, this is not necessary in every embodiment. While it is advantageous to use only the data collected during this time period, the applicant has also discovered that good results can still be achieved if the data is measured while the user is moving. Furthermore, it is not necessary in every embodiment to look preferentially at movement in the personal axis. In some embodiments, for example in modifications of the embodiments described above where the data relates entirely to movement during the measurement window in which the first individual is required to keep their hand substantially steady and/or substantially stationary, it is possible for the data to relate to just translational movement or just to rotational movement or to a combination of translational and rotational movement, as such movement will represent hand tremor.

Although embodiments described above are in the context of a test, this is not necessary in every embodiment. For example, relevant data can be collected without a test and/or without using an output to the first individual at all. It is also not necessary to have a user input other than the measurement unit. One of the discoveries of the inventors is that the first individual's hand movement in the personal axis can provide relevant information that can be used in determining their cognitive state: the data can be gathered in various ways. Preferably, the user is holding the mobile device while the data is gathered, most preferably with both hands and most preferably in front of them while sitting or standing, as would generally be the case for the embodiments described in detail above. Furthermore, where the data to be used are data relating to movements during a measurement window in which the hand is held substantially steady and/or substantially stationary, it is preferable for the apparatus, for example on the mobile device, to have an output and the apparatus is configured to indicate to the first individual via the output when he/she is required to keep his/her hand substantially steady and/or substantially stationary. This does not necessarily need to be done explicitly, but can be done in the form of a task as in the above embodiments.

Although in the embodiments described above, the measurement unit is an IMU in a mobile device, this is not essential in every embodiment. Any measurement device which is able to measure the first individual's hand movement in the personal axis can be used. Therefore, a mobile device is not necessary in every embodiment.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in Switzerland patent application number 00083/21 and U.S. patent application No. 63/211,960, from which this application claims priority, and in the abstract accompanying this application, are incorporated herein by reference.

REFERENCE NUMBERS OR SIGNS USED IN THE FIGURES

1 Apparatus
2 Mobile device
3 First camera
3.1 View direction of the first camera
4 Second camera
4.1 View direction of the second camera
5 Output means
5.1 Optical output means
5.2 Audio output module
6 IMU
6.1 Accelerometer
6.2 Gyroscope
6.3 Path module
7, 7' Task module
15 8, 8', 8" Feature extraction module
9, 9', 9" Machine learning module
10 Input means
10.1 Input element
12 Output view direction of the optical output means
13 Microphone
14, 14' Augmented reality module
15, 15' Enabling module
16, 16' Recording module
θ Pitch
Φ Roll
φ Heading
AR Augmented Reality
PE Physical Environment
TP Target Position
VO Virtual Object
VE Virtual element (ring)
X, Y, Z Orthogonal (positive) axes
XB, YB, ZB Orthogonal (negative) axes As the skilled person will appreciate, according to aspects of the invention, an apparatus, method or computer program, specific embodiments of which are described above, can be provided in accordance with any of the following clauses.

1. Apparatus (1) for determining a cognitive state of a user of a mobile device (2), the apparatus (1) comprising: the mobile device (2),
   an IMU (6) in the mobile device (2),
   optical output means (5.1) in the mobile device (2), for optically giving out information to the user,
   a camera (3) in the mobile device (2), for recording images of an environment of the mobile device (2),
   an augmented reality module (14), for generating an augmented reality environment (AR) shown via the optical output means (5.1) and based on the environment (PE) of the mobile device (2) captured by the camera (3),
   characterised in that the apparatus (1) further comprises
   an enabling module (15), for enabling an input element (10.1) in the mobile device (2) once the augmented reality environment is shown, said enabling depending on data measured by the IMU (6), said input element (10.1) allowing the user to solve a task once it is selected by the user after being enabled
   a recording module (16), for recording data from the IMU (6) in a period of time between the input element (10.1) enablement and selection,
   a feature extraction module (8), for reducing the data recorded by the recording module to a set of magnitudes at given frequencies,
   a machine learning module (9), for determining the cognitive state of the user based on said set of magnitudes at given frequencies.
2. The apparatus (2) of clause 1, wherein said period of time is comprised between 1.20 seconds and 1.40 seconds, and it is preferably equal to 1.28 seconds.
3. The apparatus (2) of any of the clauses 1 or 2, wherein said set of magnitudes at given frequencies comprises N frequencies, wherein N is an integer number between 7 and 15, preferably N=10.
4. The apparatus (2) of any of the clauses 1 to 3, wherein said given frequencies are all lower than 10 Hz.
5. The apparatus (2) of any of the clauses 1 to 4, wherein the frequency resolution of said set of magnitudes at given frequencies is the inverse of said period of time.
6. The apparatus (2) of any of the clauses 1 to 5, wherein said given frequencies are 0.78, 1.56, 2.34, 3.12, 3.91, 4.69, 5.47, 6.25, 7.03, 7.81.
7. The apparatus (2) of any of the clauses 1 to 6, the enabling module (14) being arranged to enable the input element (10.1) when the acceleration measured by the accelerometer is below a threshold, said threshold being for example 4.5 $m/s^2$.
8. The apparatus (2) of any of the clauses 1 to 7, the enabling module (14) being arranged to enable the input element (10.1) depending on at least one image taken by the camera (3).
9. The apparatus (2) of clause 8, the enabling module (14) being arranged to enable the input element (10.1) depending on the presence of a determined element in at least one image taken by the camera (3).
10. The apparatus (2) of any of the clauses 1 to 9, wherein the IMU (6) comprises preferably an accelerometer (6.1), for measuring the locational change of the mobile device (2), and/or a gyroscope (6.2), for measuring the orientation change of the mobile device (2).
11. The apparatus (2) of any of the clauses 1 to 10, comprising a path module (6.3) arranged for determining a positional path of the mobile device (2) in the environment, wherein the machine learning module (9) is arranged for determining the cognitive state of the user based also on the positional path of the mobile device (2), for example as determined while the user solves the task.
12. The apparatus (2) of any of the clauses 1 to 11, wherein the augmented reality module (14) is arranged to augment the visualization of the 5 surrounding once the user is at a predetermined distance, for example at 30 cm, to a target position (TP).
13. Method for determining a cognitive state of a user of a mobile device (2), by using an apparatus (1) comprising:
   the mobile device (2),
   an IMU (6) in the mobile device (2),
   optical output means (5.1) in the mobile device (2), for optically giving out information to the user,
   wherein the method comprises the following steps
   recording images of an environment of the mobile device (2), said images being taken by using a camera (3) in the mobile device (2),
   generating an augmented reality environment shown via the optical output means (5.1) and based on the environment of the mobile device (2) captured by the camera (3), by using an augmented reality module (14) of said apparatus (1),
   enabling an input element (10.1) in the mobile device (2) once the augmented reality environment is shown, said enabling depending on data measured by the IMU (6), said input element (10.1) allowing the user to solve a task once it is selected by the user after being enabled, by using an enabling module (15) of said apparatus (1), recording data from the IMU (6) in a period of time between the input element enablement and selection, by using a recording module (16) of said apparatus, reducing the data recorded by the recording module (16) to a set of magnitudes at given frequencies, by using a feature extraction module (8) of said apparatus, determining the cognitive state of the user based on said set of magnitudes at given frequencies, by using a machine learning module (9) of said apparatus (1).

14. Computer program for determining a cognitive state of a user of a mobile device (2) including instructions configured to perform the following steps, when the instructions are executed on a processor of the apparatus (1) and/or of the mobile device (2):

recording images of an environment of the mobile device (2), said images being taken by using a camera (3) in the mobile device (2), generating an augmented reality environment shown via optical output means (5.1) of the mobile device (2) and based on the environment of the mobile device (2) captured by the camera (3), by using an augmented reality module (14) of said apparatus (1), enabling an input element (10.1) in the mobile device (2) once the augmented reality environment is shown, said enabling depending on data measured by an IMU (6) of the mobile device (2), said input element (10.1) allowing the user to solve a task once it is selected by the user after being enabled, by using an enabling module (15) of said apparatus (1), recording data from the IMU (6) in a period of time between the input element enablement and selection, by using a recording module (16) of said apparatus (1), reducing the data recorded by the recording module (16) to a set of magnitudes at given frequencies, by using a feature extraction module (8) of said apparatus, determining the cognitive state of the user based on said set of magnitudes at given frequencies, by using a machine learning module (9) of said apparatus (1).

The invention claimed is:

1. Apparatus for providing information relating to a cognitive state of a first individual, the apparatus comprising:

A mobile device, a measurement unit operable to measure the first individual's hand movement in a personal axis, the personal axis being an axis from the hand to the first individual, wherein the first individual is a user of the mobile device, and the measurement unit is an IMU in the mobile device, a recording module configured to record data from the measurement unit, a machine learning module configured to provide information relating to the cognitive state of the first individual using a set of first movement data based on the data recorded by the recording module, wherein the set of first movement data relates to movement of the hand of the first individual in the personal axis over movement of the hand of the first individual in axes orthogonal to the personal axis, an optical output means in the mobile device, for optically giving out information to the user, a camera in the mobile device, for recording images of an environment of the mobile device, an augmented reality module, for generating an augmented reality environment shown via the optical output means and based on the environment of the mobile device captured by the camera, an enabling module, for enabling an input element in the mobile device once the augmented reality environment is shown, said enabling depending on data measured by the IMU, said input element allowing the user to solve a task once it is selected by the user after being enabled.

2. The apparatus of claim 1, wherein the machine learning module is trained on sets of second movement data associated with a plurality of second individuals, each set of second movement data being associated with a particular second individual, each second individual being identified as having a medical condition or not having the medical condition, the plurality of second individuals including at least one individual identified as having the medical condition and at least one individual identified as not having the medical condition, the medical condition being Alzheimer's disease and/or Mild Cognitive Impairment, wherein each of the sets of second movement data relates to movement of a respective hand of the respective individual in a respective personal axis over movement of the respective hand in axes orthogonal to the respective personal axis, the respective personal axis being an axis from the respective hand to the respective individual.

3. The apparatus of claim 1, including a feature extraction module configured to extract, from the data recorded by the recording module, data relating to movement of the hand of the first individual in the personal axis, to form the set of first movement data.

4. The apparatus of claim 3, wherein the IMU includes a gyroscope for measuring the orientation change of the mobile device, and the feature extraction module is configured to utilise data recorded by the recording module relating to the orientation change of the mobile device to extract, from the data recorded by the recording module, data relating to movement of the hand of the first individual in the personal axis, to form the set of first movement data.

5. The apparatus of claim 1, wherein the recording module is configured to record data from the IMU in a period of time between the input element enablement and selection.

6. The apparatus of claim 1, wherein the apparatus is configured to require, during a measurement window, the first individual to restrict all movements of the hand except in the personal axis, wherein the set of first movement data is substantially entirely based on data relating to movement during the measurement window.

7. The apparatus of claim 1, wherein the apparatus is configured to require, during a measurement window, the first individual to keep the hand substantially steady and/or substantially stationary, wherein the set of first movement data is substantially entirely based on data relating to movement during the measurement window; wherein the apparatus includes an output and the apparatus is configured to indicate to the first individual via the output when the first individual is required to keep the hand substantially steady and/or substantially stationary.

8. The apparatus of claim 1, wherein the measurement unit includes an accelerometer and the apparatus includes an integration module configured to integrate the data recorded by the recording module resulting from the accelerometer, wherein the set of first movement data is based on the integrated data.

9. The apparatus of claim 8, wherein the integration module is configured to double-integrate the data recorded by the recording module resulting from the accelerometer to result in positional data, wherein the set of first movement data is based on the positional data.

10. The apparatus of claim 1, comprising a feature extraction module configured to reduce the data recorded by the recording module to a set of magnitudes at given frequencies, wherein the set of first movement data is based on said set of magnitudes at given frequencies.

11. A method of providing information relating to a cognitive state of a first individual, including:

using a machine learning module to provide information relating to the cognitive state of the first individual using a set of first movement data relating to movement of a hand of the first individual, wherein the set of first movement data relates to movement of the hand of the first individual in the personal axis over movement of the hand of the first individual in axes orthogonal to the personal axis, the personal axis being an axis from the hand to the first individual, wherein obtaining the first set of movement data comprises using an apparatus comprising:

a mobile device, an IMU in the mobile device, an optical output means in the mobile device, for optically giving out information to the user, and wherein the method comprises the following steps:

recording images of an environment of the mobile device, said images being taken by using a camera in the mobile device, generating an augmented reality environment shown via the optical output means and based on the environment of the mobile device captured by the camera, by using an augmented reality module of said apparatus, enabling an input element in the mobile device once the augmented reality environment is shown, said enabling depending on data measured by the IMU, said input element allowing the user to solve a task once it is selected by the user after being enabled, by using an enabling module of said apparatus, recording data from the IMU in a period of time between the input element enablement and selection, by using a recording module of said apparatus.

12. The method of claim 11, including using the machine learning module to predict future Alzheimer's disease and/or conversion from Mild Cognitive Impairment to Alzheimer's disease for the first individual.

13. The method of claim 11, including measuring movement of the hand of the first individual to determine the set of first movement data.

14. The method of claim 11, including requiring, during a measurement window, the first individual to keep the hand substantially steady and/or substantially stationary and/or requiring, during a or the measurement window, the first individual to restrict all movements of the hand except in the personal axis;

wherein the set of first movement data is substantially entirely based on data relating to movement during the measurement window.

15. A program configured to perform the method of claim 11 when executed on a computing device.

16. A computer implemented system for providing information relating to a cognitive state of a first individual, including:

a mobile device, a measurement unit operable to measure the first individual's hand movement in a personal axis, the personal axis being an axis from the hand to the first individual, wherein the first individual is a user of the mobile device, and the measurement unit is an IMU in the mobile device, a recording module configured to record data from the measurement unit, a machine learning module configured to provide information relating to the cognitive state of the first individual using a set of first movement data, wherein the set of first movement data relates to movement of a hand of the first individual in the personal axis over movement of the hand of the first individual in axes orthogonal to the personal axis, the personal axis being an axis from the hand to the first individual, an optical output means in the mobile device, for optically giving out information to the user, a camera in the mobile device, for recording images of an environment of the mobile device, an augmented reality module, for generating an augmented reality environment shown via the optical output means and based on the environment of the mobile device captured by the camera, an enabling module, for enabling an input element in the mobile device once the augmented reality environment is shown, said enabling depending on data measured by the IMU, said input element allowing the user to solve a task once it is selected by the user after being enabled.

17. The system of claim 16 wherein the set of first movement data is substantially entirely based on data relating to movement during a measurement window in which the first individual is required to keep the hand substantially steady and/or substantially stationary.

* * * * *